(12) United States Patent
Mijers

(10) Patent No.: US 6,932,110 B2
(45) Date of Patent: Aug. 23, 2005

(54) UNIDIRECTIONAL VALVE APPLIANCE

(75) Inventor: Jan W. M. Mijers, Venlo (NL)

(73) Assignee: Filtertek Inc., Hebron, IL (US)

( * ) Notice: Subject to any disclaimer, the term of this patent is extended or adjusted under 35 U.S.C. 154(b) by 291 days.

(21) Appl. No.: 10/428,370

(22) Filed: May 2, 2003

(65) Prior Publication Data
US 2005/0016596 A1 Jan. 27, 2005

Related U.S. Application Data

(63) Continuation of application No. PCT/EP03/04017, filed on Apr. 17, 2003.

(30) Foreign Application Priority Data

May 3, 2002 (DE) .......................... 102 19 994

(51) Int. Cl.[7] ........................... F16K 15/14; A61M 5/14
(52) U.S. Cl. .................................... 137/512.4; 604/247
(58) Field of Search .................... 137/510, 512.3, 137/512.4; 604/9, 30, 247

(56) References Cited

U.S. PATENT DOCUMENTS

| | | | | |
|---|---|---|---|---|
| 2,630,874 A | * | 3/1953 | Langdon | ................... 137/512.4 |
| 2,758,609 A | | 8/1956 | Dickert et al. | |
| 2,980,032 A | * | 4/1961 | Schneider | ................. 137/512.4 |
| 3,084,707 A | | 4/1963 | Frye | |
| 3,238,056 A | | 3/1966 | Pall | |
| 3,270,771 A | | 9/1966 | Morgan et al. | |
| 3,599,657 A | | 8/1971 | Maldavs | |
| 3,633,605 A | | 1/1972 | Smith | |
| 3,658,183 A | | 4/1972 | Best et al. | |
| 3,779,274 A | | 12/1973 | Kelly | |
| 3,782,083 A | | 1/1974 | Rosenberg | |
| 3,932,153 A | | 1/1976 | Byrns | |
| 3,966,520 A | | 6/1976 | Fallenbeck et al. | |
| 4,089,349 A | | 5/1978 | Schenk | |
| 4,141,379 A | | 2/1979 | Manske | |
| 4,148,732 A | | 4/1979 | Burrow et al. | |
| 4,181,477 A | * | 1/1980 | Litt | .......................... 137/512.4 |
| 4,237,880 A | | 12/1980 | Genese | |
| 4,241,756 A | | 12/1980 | Bennett et al. | |
| 4,343,305 A | | 8/1982 | Bron | |

(Continued)

FOREIGN PATENT DOCUMENTS

| | | |
|---|---|---|
| DE | 667 675 | 4/1934 |
| DE | GM 1 695 553 | 3/1953 |
| DE | GM 1 675 370 | 2/1954 |
| DE | 2 502 673 A1 | 7/1976 |
| DE | 29 19 343 A1 | 11/1980 |

(Continued)

OTHER PUBLICATIONS

Christians, Rolf, "Membranen inder Pneumatik," *Fluid*, pp. 39–46 (Apr. 1980).

*Primary Examiner*—John Rivell
(74) *Attorney, Agent, or Firm*—Brinks Hofer Gilson & Lione

(57) ABSTRACT

The invention relates to a unidirectional valve appliance, in particular a low pressure check valve for use for an infusion comprising a housing with an inlet and an outlet, and with at least one gasket in a pressure chamber. To prevent air entry into the infusion fluid circuit, the appliance includes an interruption of the flow by means of a static vacuum to the inlet and/or outlet or excess pressure at the outlet. This ensures in reliable manner that a flow of the infusion fluid in a reliable manner only when a static excess pressure differential is exposed to the inlet.

21 Claims, 8 Drawing Sheets

U.S. PATENT DOCUMENTS

| | | | |
|---|---|---|---|
| 4,355,639 A | * 10/1982 | Di Salvo | 137/510 |
| 4,404,006 A | 9/1983 | Williams et al. | |
| 4,415,003 A | 11/1983 | Paradis et al. | |
| 4,459,139 A | 7/1984 | vonReis et al. | |
| 4,534,764 A | 8/1985 | Mittleman et al. | |
| 4,556,086 A | 12/1985 | Raines | |
| 4,593,720 A | 6/1986 | Bergandy | |
| 4,598,661 A | 7/1986 | Roe | |
| 4,646,781 A | 3/1987 | McIntyre et al. | |
| 4,664,800 A | 5/1987 | Raines et al. | |
| 4,670,510 A | 6/1987 | Kobayashi et al. | |
| 4,712,583 A | 12/1987 | Pelmulder et al. | |
| 4,749,003 A | 6/1988 | Leason | |
| 4,768,547 A | 9/1988 | Danby et al. | |
| 4,846,215 A | 7/1989 | Barree | |
| 4,874,513 A | 10/1989 | Chakraborty et al. | |
| 4,966,199 A | 10/1990 | Ruschke | |
| 4,986,904 A | 1/1991 | Bugar et al. | |
| 5,011,555 A | 4/1991 | Sager | |
| 5,025,829 A | 6/1991 | Edwards et al. | |
| 5,147,545 A | 9/1992 | Despard et al. | |
| 5,215,538 A | 6/1993 | Larkin | |
| 5,230,727 A | 7/1993 | Pound et al. | |
| 5,269,917 A | 12/1993 | Stankowski | |
| 5,443,723 A | 8/1995 | Stankowski et al. | |
| 5,453,097 A | 9/1995 | Paradis | |
| 5,500,003 A | 3/1996 | Guala et al. | |
| 5,520,661 A | 5/1996 | Lal et al. | |
| 5,603,792 A | 2/1997 | Guala et al. | |
| 5,617,897 A | 4/1997 | Myers | |
| 5,749,861 A | 5/1998 | Guala et al. | |
| 5,771,935 A | 6/1998 | Myers | |
| 5,935,100 A | 8/1999 | Myers | |
| 6,086,762 A | 7/2000 | Guala | |
| 6,168,653 B1 | 1/2001 | Myers | |
| 6,290,682 B1 | 9/2001 | Myers | |

FOREIGN PATENT DOCUMENTS

| | | |
|---|---|---|
| DE | 30 35 301 A1 | 4/1981 |
| DE | GM 82 14 927.5 | 9/1982 |
| DE | 32 15 329 A1 | 12/1982 |
| DE | GM 86 03 917 U1 | 5/1986 |
| DE | 36 32 412 A1 | 3/1988 |
| DE | 38 03 380 | 8/1989 |
| DE | 40 39 814 A1 | 6/1992 |
| DE | GM 92 09 491.0 | 10/1992 |
| DE | 41 42 494 A1 | 7/1993 |
| DE | 42 01 258 A1 | 7/1993 |
| DE | GM 93 19 810.8 U1 | 3/1994 |
| DE | 43 09 262 A1 | 6/1994 |
| DE | 43 04 949 A1 | 8/1994 |
| DE | GM 93 10 673.4 | 9/1994 |
| DE | 29 501 239 | 4/1995 |
| DE | 196 05 217 | 2/1996 |
| DE | GM 296 10 419.1 | 12/1996 |
| DE | 195 45 421 A1 | 6/1997 |
| DE | 2 713 618 C2 | 10/1997 |
| DE | 196 43 360 C1 | 5/1998 |
| DE | 197 49 562 C1 | 4/1999 |
| EP | 0 072 800 B1 | 3/1983 |
| EP | 0 562 246 A1 | 9/1993 |
| EP | 0 612 537 A3 | 8/1994 |
| EP | 0 612 537 A2 | 8/1994 |
| EP | 0 652 018 B1 | 10/1996 |
| EP | 0 812 596 A1 | 12/1997 |
| EP | 0 878 628 A2 | 11/1998 |
| EP | 0 887 085 A2 | 12/1998 |
| EP | 0 934 757 A2 | 8/1999 |
| FR | 2 666 745 A | 3/1992 |
| GB | 811 818 | 4/1959 |
| GB | 2 027 168 A | 2/1980 |
| WO | WO 88/02639 | 4/1988 |
| WO | WO 89/02764 | 4/1989 |
| WO | WO 91/11641 | 8/1991 |
| WO | WO 96/03166 | 2/1996 |
| WO | WO 97/03712 | 2/1997 |
| WO | WO 97/47339 | 12/1997 |

* cited by examiner

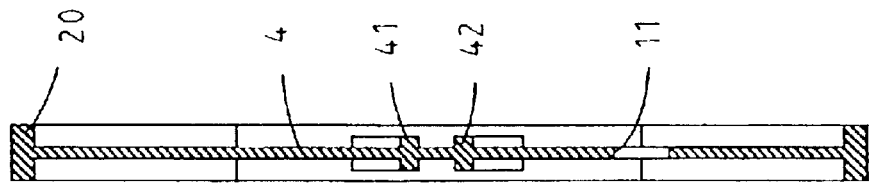
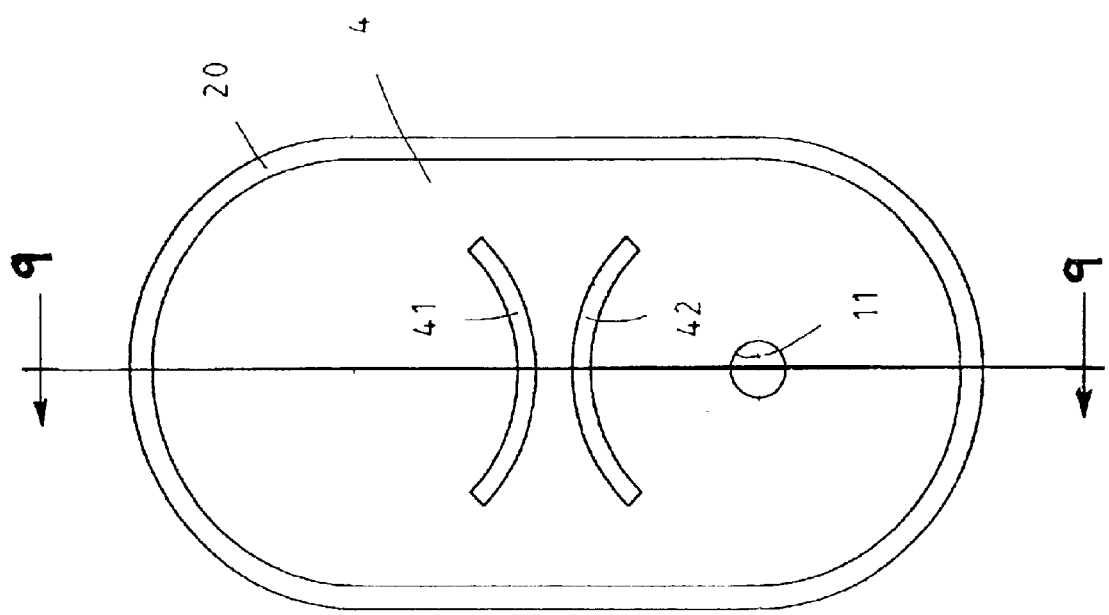

UNIDIRECTIONAL VALVE APPLIANCE

Applicant claims, under 35 U.S.C. §§ 119, 120 and 365, the benefit of priority of the filing date of May 3, 2002 of German patent application DE 102 19 994.9 and this application is a continuation of Patent Cooperation Treaty patent application, Ser. No. PCT/EP03/04017, filed on Apr. 17, 2003, that designates the United States, among other countries, and was not published under PCT Article 21(2) in English. Patent Cooperation Treaty patent application Ser. No. PCT/EP03/04017 in turn claims the benefit of foreign priority based on the aforementioned German patent application No. DE 102 19 994.9, filed on May 3, 2002.

FIELD OF INVENTION

The invention relates to a unidirectional valve appliance, in particular a low pressure check valve for use in an infusion set, comprising a housing with an inlet and an outlet and at least one gasket in a pressure chamber.

BACKGROUND OF THE INVENTION

Check valve appliances are used preferably for infusion instruments in hospitals, whereby the valve appliance is used for the purpose of bringing about an immediate stop to fluid when a dispenser filled with infusion fluid runs dry so that no air gets into the infusion fluid and into the venous system of a patient. A valve appliance for use in an infusion instrument is for example known from the German published application DE 29 19 343 A1, which is equipped with a drip chamber and a float valve, and which prevents the entry of air into the infusion hose when the chamber runs dry, whereby on the exit side in the flexible line leading to the infusion needle a roller clamp is arranged. To prevent a filling of the entire line system with air, a double-seat float valve is used with a float ball. Such floating ball valves, however, do not always respond exactly, so that entry of air into the infusion hose may not be prevented in every case.

A further check valve device is known from the German published application DE 36 32 412 A1, in which a valve is arranged in front of a drip chamber in the direction of flow. A floating ball is adjacent to the channel wall under friction during sealing and cannot prevent air supply with absolute certainty in the corresponding range of motion.

From DE 197 49 562 A1 an infusion instrument is further known which consists of a high suspended container for the infusion fluid as well as an IV stand that can be connected to a throttle container by means of a tribolet tube, an adjustable roller clamp underneath on a flexible inlet tube and an injection needle located at the end of the tube. To prevent the penetration of air into the infusion fluid, in particular at the end of the infusion fluid, in the direction of flow before the drip chamber or at its entrance, a built-in valve is provided that depends upon the static pressure of the infusion fluid flow. However, in practice there is the possibility of interchanging the terminals of the valve through carelessness and thus the function of the valve is no longer guaranteed. This becomes particularly dangerous if air penetrates into the system, which, in case the air penetrates all the way to the veins, can result in an embolism for the patient. It is therefore important that no air mixes in with the infusion fluid, which results in the above mentioned disadvantage. One particular disadvantage is that this aforementioned valve may prevent the penetration of air into the system where there is an excess static pressure at the outlet.

Accordingly, there is a need for a check valve with low opening pressure which can be used for an infusion set and assembly thereof with gravitational pressure and/or pump pressure and which prevents the penetration of air into the system of the infusion set and assembly thereof with high certainty.

BRIEF SUMMARY OF THE INVENTION

A unidirectional valve appliance, and in particular a check valve assembly has been invented which provides the foregoing and following advantages and meets the above and below described needs, among others.

Preferred embodiments of the invention have the advantage of providing an effective check valve that interrupts the flow when there is a static vacuum to the inlet and/or outlet, or when there is excess pressure at the outlet, and thus the penetration of air into the system of the infusion instrument is avoided. A static vacuum at the inlet can, for example, occur when a dispenser of the infusion fluid has run dry, when an infusion pump is working defectively, or air has entered into the system. An excess pressure at the outlet tube can, for example, occur during a temporary occlusion of the arm veins of the patient when a medicine pump is additionally connected, and this excess pressure could result in the medicine being pumped into the gravity infusion instrument and away from the patient.

Preferred embodiments of the invention may also have the advantage of reliably stopping further transport of infusion fluid, and thus the penetration of air-enriched infusion fluid into the veins is prevented. Additionally, by means of the unidirectional valve appliance it is assured that when excess pressure from an infusion or medicine pump occurs at the outlet, the valve closes and thus the medicine does not go into the infusion instrument, preventing a short-term discontinuity in medicine dosage.

In one aspect of the invention, a low pressure check valve for use in an infusion set having infusion fluid is provided comprising a first housing half having an inlet and first lipped sealing ring, the exterior of the first lipped sealing ring in communication with the inlet; a second housing half having an outlet and second lipped sealing ring, the interior of the second lipped sealing ring in communication with the outlet; a gasket with a first portion overlying the first lipped sealing ring and having at least one opening communicating with the interior of the first lipped sealing ring, and another portion overlying the second lipped sealing ring; means for sealing the first and second housing halves together and clamping the gasket portions therebetween; and means for tensioning the gasket portions over the first lipped sealing ring and the second lipped sealing ring, thereby forming a pressure chamber in communication with the second lipped sealing ring exterior and the first lipped sealing ring interior via the one or more gasket openings; whereby infusion fluid flow in the pressure chamber is interrupted by the gasket portion engaging the first lipped sealing ring when the fluid pressure at the inlet is less than the fluid pressure of the pressure chamber, or by the gasket portion engaging the second lipped sealing ring when the fluid pressure at the outlet is less than the fluid pressure of the pressure chamber, or by the gasket portion engaging the first lipped sealing ring when there is a higher pressure at the outlet and pressure chamber as compared to the pressure at the inlet.

Preferred embodiments of the invention have the distinct advantage of providing a check valve that, upon the presence of a vacuum at the inlet or outlet, or in the case of an excess pressure at the outlet, a certain stoppage of the infusion fluid is assured. Other advantages of the invention include, among other things, a simple assembly option of the valve gasket, in particular with the design of a t-shaped attachment or the like, which comes to lie in a corresponding recess of the housing halves, so that a permanent and secure function of the valve appliance occurs.

Other features and advantages of the present invention will become more fully apparent from the following description of the preferred embodiments, the appended claims, and the accompanying drawings.

BRIEF DESCRIPTION OF SEVERAL VIEWS OF THE DRAWINGS

FIG. 8 is a planar view of a gasket.

FIG. 9 is a cross-sectional view of FIG. 8 along line 9—9.

DETAILED DESCRIPTION OF EMBODIMENTS OF THE INVENTION

Figure 1:
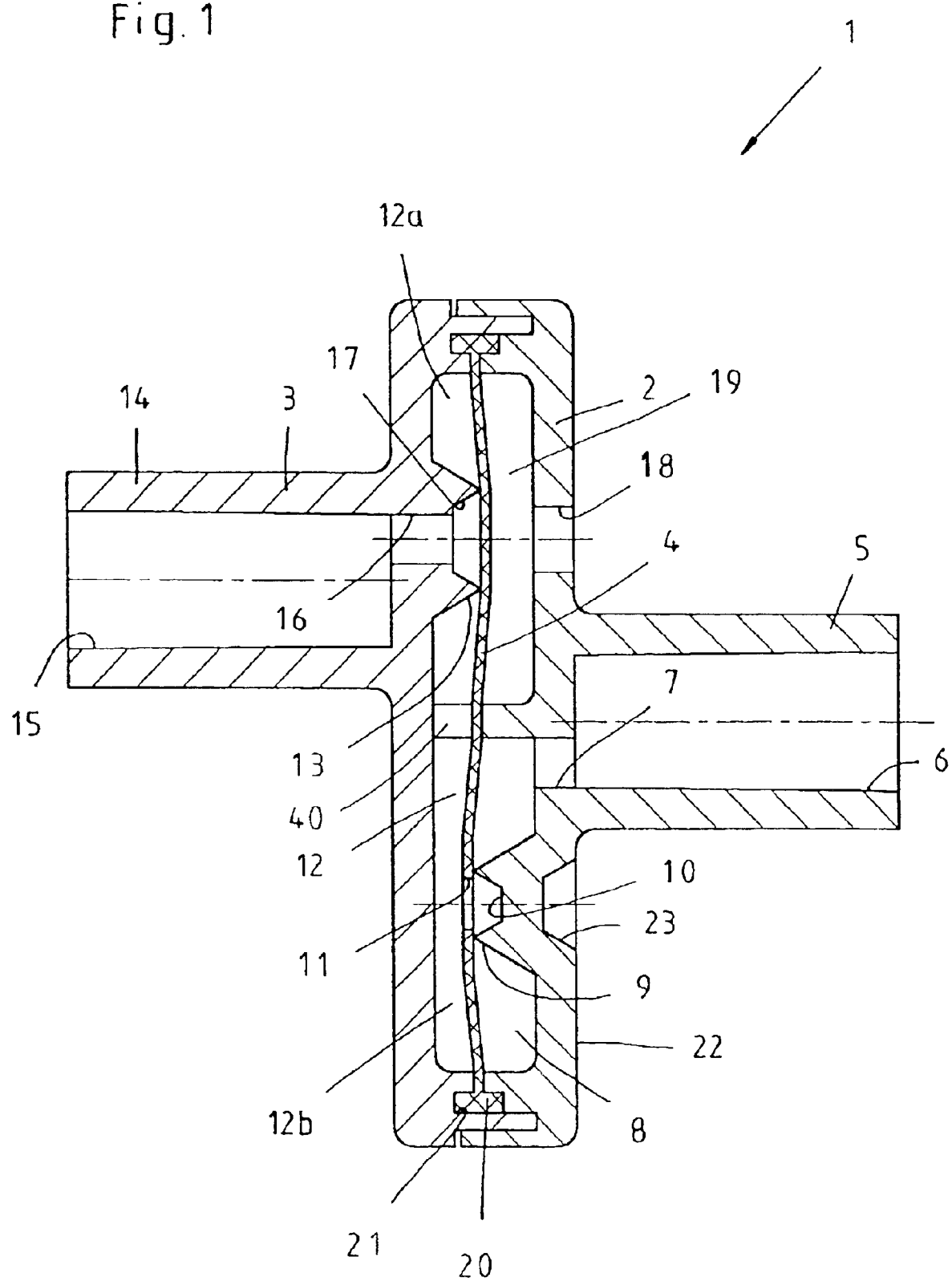
FIG. 1 is an embodiment of the valve appliance in a cross-sectional view.

FIG. 1 shows a valve apparatus 1 according to the invention, consisting of a first housing half 2 and a second housing half 3 as well as a gasket 4 between the housing halves 2, 3 when assembled. The gasket 4 is wedged or clamped between the two housing halves 2, 3. The first housing half 2 includes an inlet tube 5 with an inlet 6, and an outlet via opening 7, which discharges into a first antechamber 8 of the housing half 2. The round or elliptically shaped annular antechamber 8 has a centrally located lipped sealing ring 9, which is with housing half 2, and has a cavity 10 within lipped sealing ring 9 (see also FIG. 2). The gasket 4 adjacent to the lipped sealing ring 9 has an opening 11, preferably arranged centrally to the lipped sealing ring 9, so that when gasket 4 is lifted from the lipped sealing ring 9, a connection to the pressure chamber 12 is made possible through the opening 11.

The pressure chamber 12 can be one pressure chamber 12 between housing halves 2, 3 or at least two pressure chambers 12a, 12b can be constructed, which are connected to each other by way of at least one junction opening 40, so that an identical static pressure prevails. The gasket 4 is adjacent to a second lipped sealing ring 13, which is with second housing half 3. The second housing half 3 has an outlet tube 14 with outlet 15, which communicates with opening 16, into the cavity 17 which is formed by the lipped sealing ring 13, so that when gasket 4 is lifted from the lipped sealing ring 13, a connection to pressure chamber 12 results. An opening 18 in the first housing half 2 exposes one side of a portion of gasket 4 to ambient atmospheric pressure by way of a second antechamber 19. The gasket 4 is secured between the two housing halves 2, 3 in such a way that in a pressureless state, where there is no pressure differential between the fluids in housing halves 2, 3, the gasket 4 is directly adjacent to the lipped sealing rings 9, 13, and overlies and abuts against sealing rings 9, 13 as shown in FIG. 1. To prevent the gasket 4 within the housing halves 2, 3 from slipping to one side or lose its preferred tensioning engagement over sealing rings 9, 13, and thus to assure a certain function of the check valve assembly 1, the gasket 4 is constructed in one piece in the embodiment depicted in FIG. 1, and has on or near its border a t-shaped, in section, attachment 20, which is located in a corresponding recess 21 of the first and second housing halves 2, 3. Alternatively, gasket 4 may be a two-piece gasket, and/or attachment 20 may be of an alternative section, such as c-shaped, L-shaped, or v-shaped.

By means of a static pressure differential, for example, from the inflowing infusion fluid of a dispenser arranged at a higher elevation into the inlet 6 through the opening 7 into the first antechamber 8, the gasket 4 is lifted from the first lipped sealing ring 9, so that the infusion fluid can flow under the gasket 4 and into the first lipped sealing ring 9 interior and cavity 10, through the gasket 4 opening 11 into the pressure chamber 12. On the basis of the increasing pressure in the pressure chamber 12, the gasket 4 is also slightly raised in the area of the second lipped sealing ring 13 exterior, so that the infusion fluid can flow through the second lipped sealing ring 13 interior and cavity 17 to opening 16 and into the outlet 15. When the static pressure differential subsides from the infusion fluid, for example, by emptying of the dispenser that supplies the check valve assembly via inlet 6, the gasket 4 immediately returns to position against the lipped sealing ring 9, so that a stop of the infusion fluid is assured.

For the case of a vacuum at the inlet 6, in addition, suctioned and pressed against the gasket 4 is the lipped sealing ring 9 and also results in a stoppage of infusion fluid flow. If a vacuum is present at the outlet tube 14 or outlet 15, the gasket 4 will also be suctioned and pressed against the second lipped sealing ring 13, so that infusion fluid flow is stopped. For the case where there is an excess pressure differential at the outlet tube 14 or outlet 15, as compared to inlet 6, the gasket 4 can be raised from the second lipped sealing ring 13, but the gasket 4 is pressed against the first lipped sealing ring 9 due to the excess fluid pressure on gasket 4 and the existing initial tension of gasket 4 over sealing ring 9, thus preventing a flow of the infusion fluid into the inlet 6. The valve appliance 1 thus makes possible a stoppage of the infusion fluid for the case that a vacuum prevails at the inlet tube 5 or a vacuum or excess pressure at the outlet tube 14, so that penetration of air into the system of the infusion instrument can be avoided. Thus, only for the case of a static excess pressure differential at the inlet tube 5 that is over that of outlet tube 14, is it possible for a flow of infusion fluid.

Figure 2:
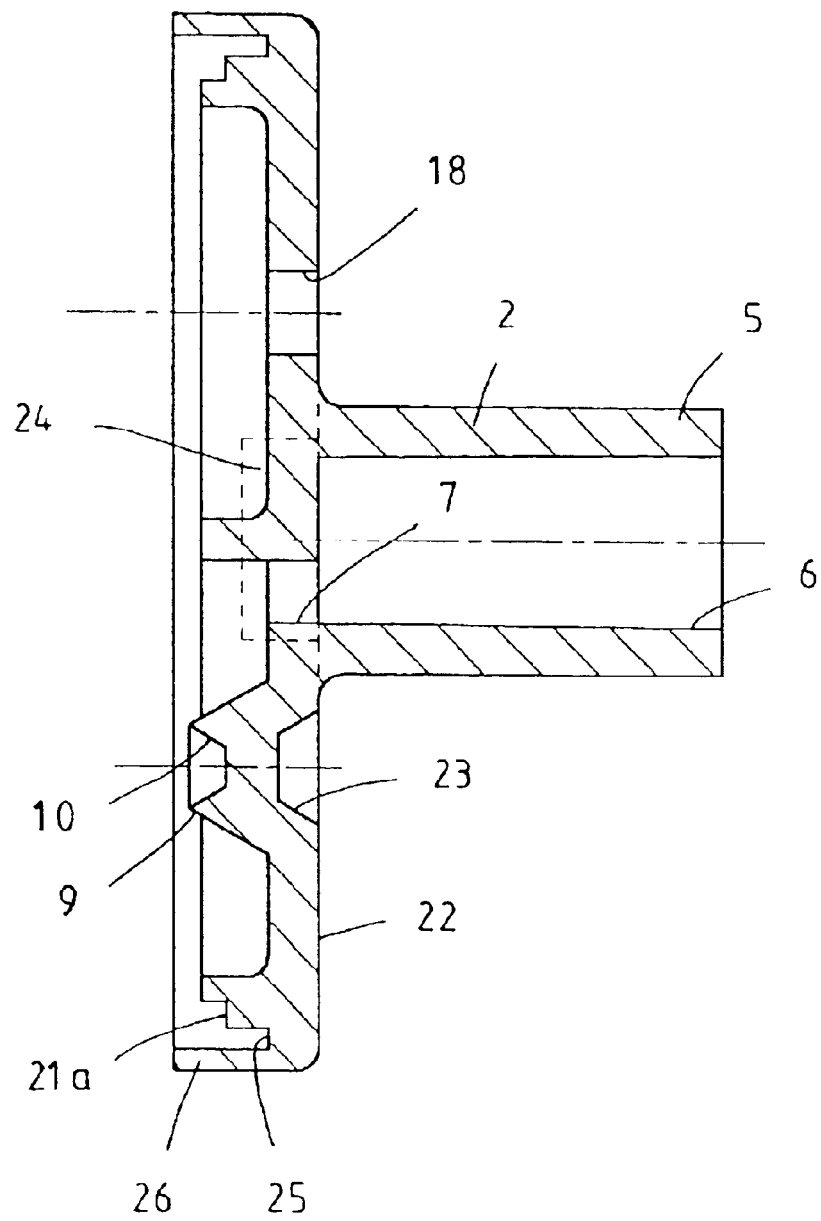
FIG. 2 is a cross-sectional view of the first housing half.

FIG. 2 shows in sectional view first housing half 2 with inlet tube 5 and inlet 6 as well as an integrally formed lipped sealing ring 9 and cavity 10. See also FIGS. 3 and 4. The housing half 2 has an oval basic form, from which the inlet tube 5 projects vertically. The housing half 2 may be constructed of plastic as a single-piece and may have on its outer surface 22 a cavity 23 in the area of the first lipped sealing ring 9 as well as optional triangular-shaped cavities 24 that are laterally offset to the inlet tube 5. A recess 21a is present for reception of an attachment, such as t-shaped attachment 20, of the gasket 4, and recess 21a may gradually change into another recess 25. The recess 25 is bounded by a collar 26 and is provided for the reception of a corresponding collar 30 of the second housing half 3.

Figure 3:
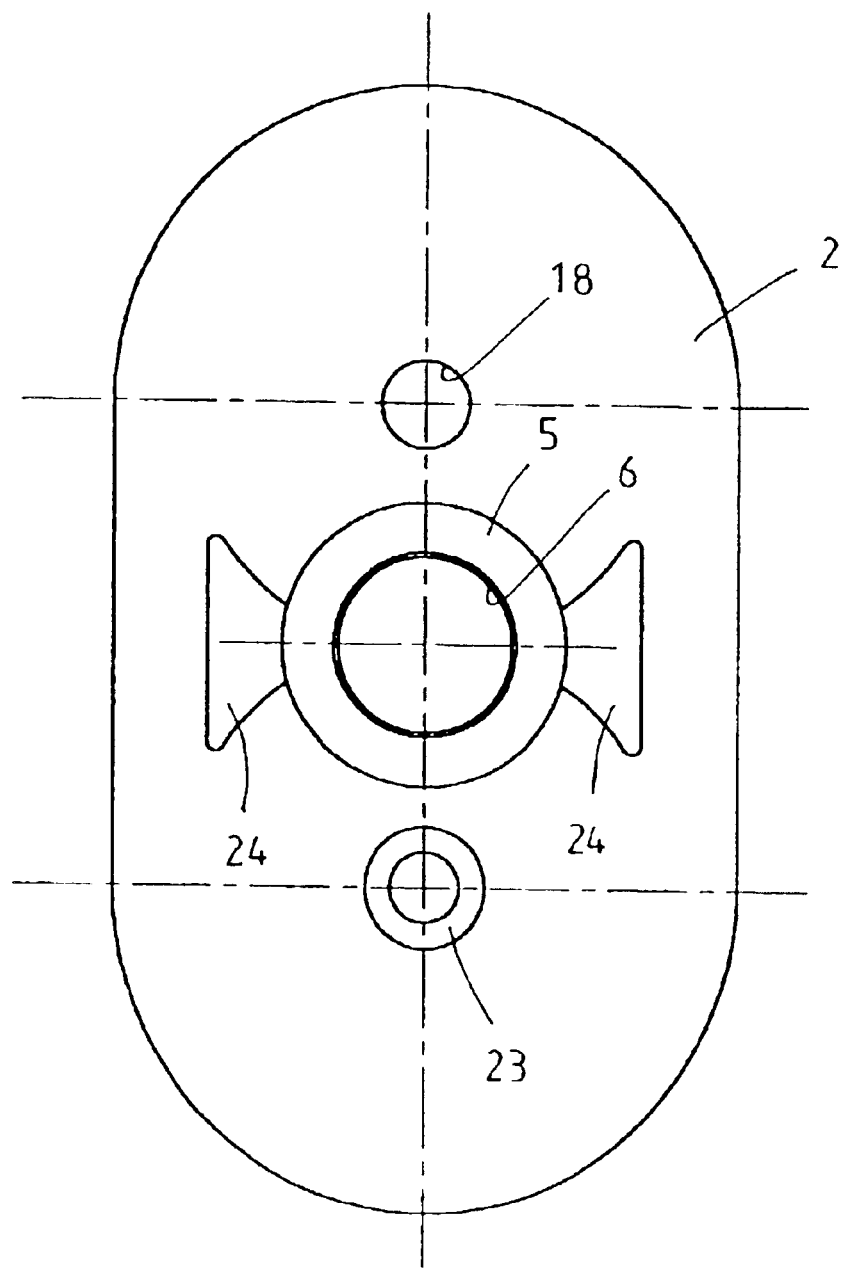
FIG. 3 is a planar view of the exterior of the housing half of FIG. 2.
Figure 4:
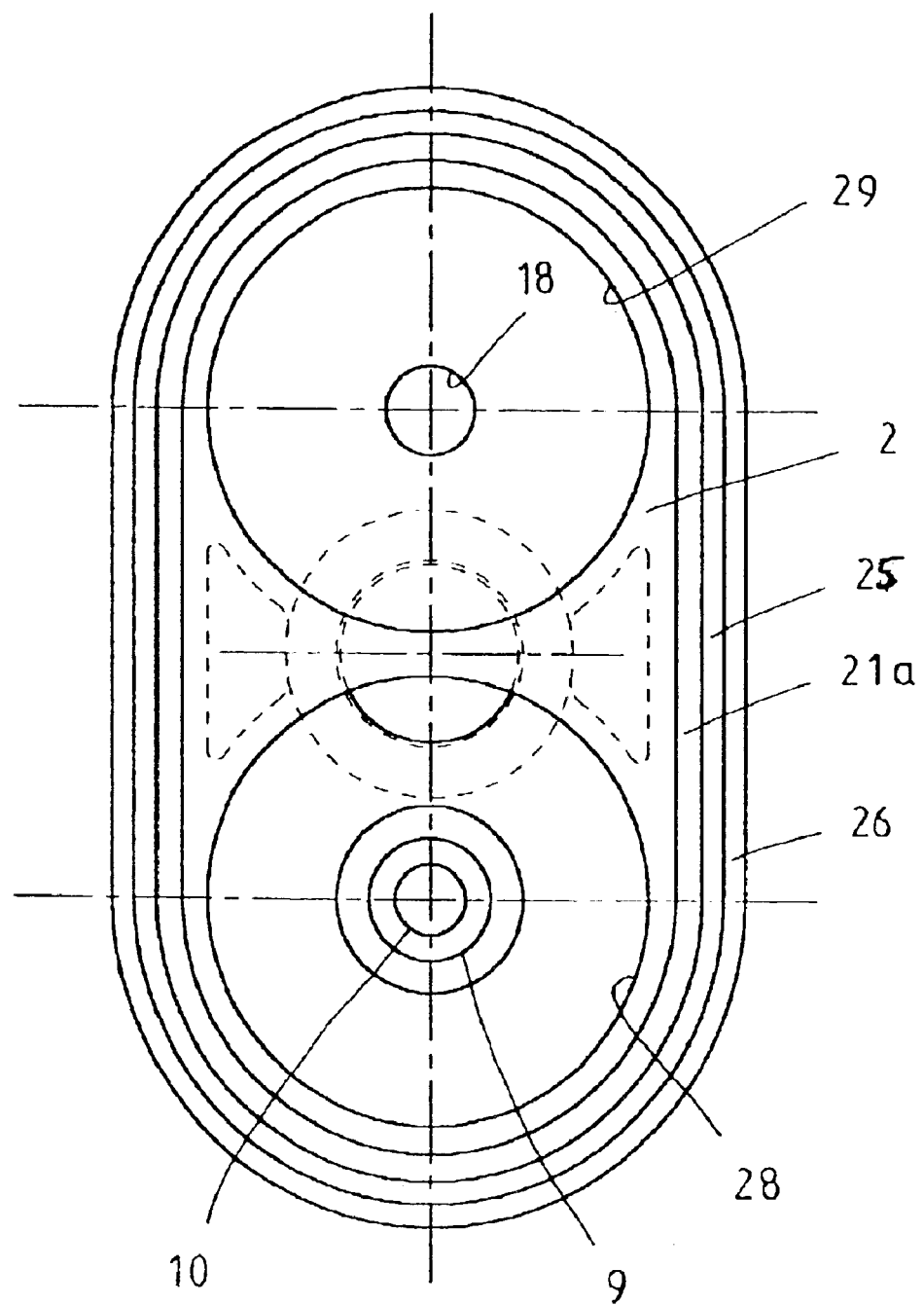
FIG. 4 is a planar view of the interior of the housing half of FIG. 2.

FIGS. 3 and 4 show planar views of the first housing half 2 exterior and interior. The antechambers 8 and 19 may be formed by ring-shaped recesses 28, 29, respectively.

Figure 5:
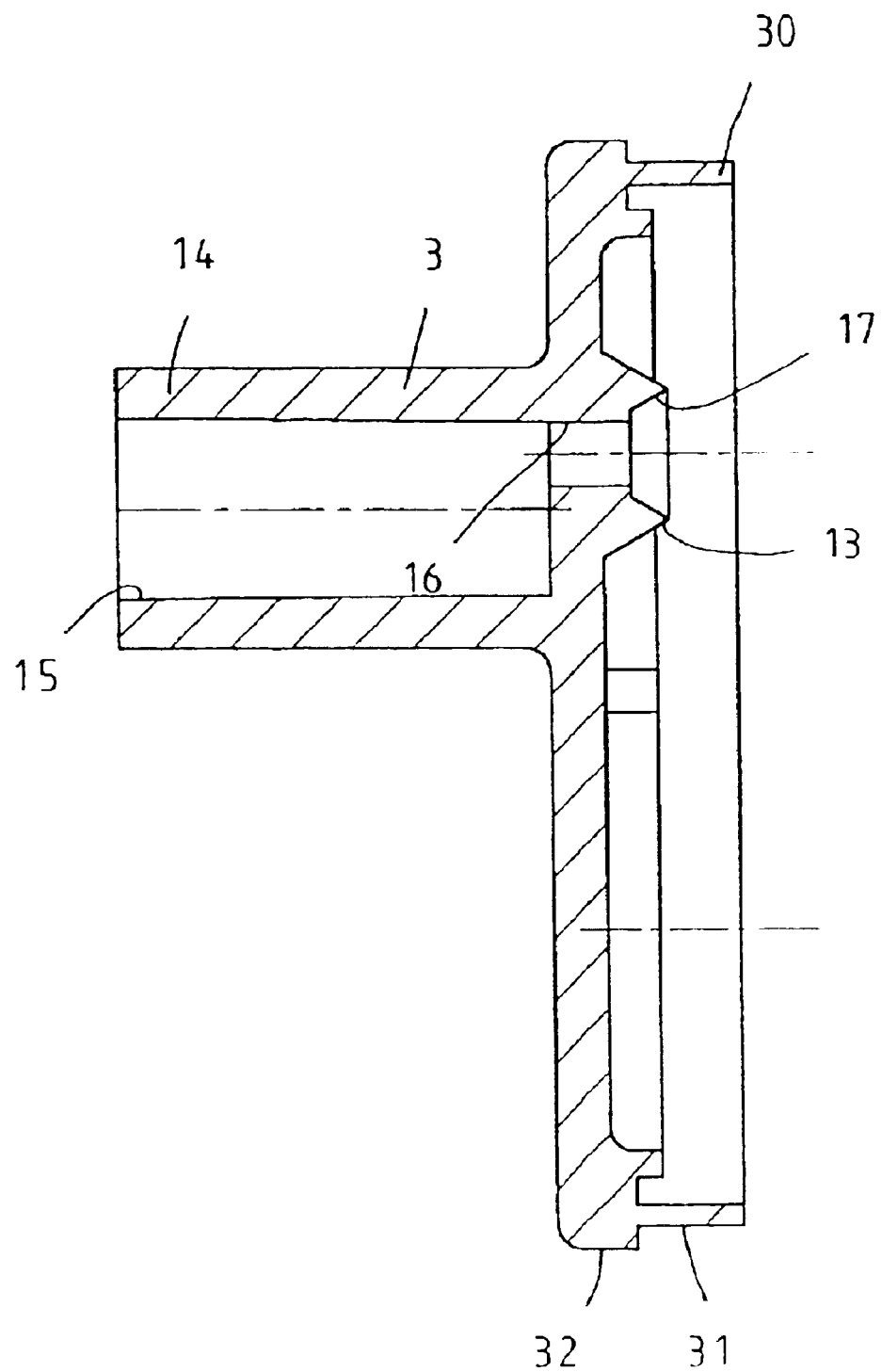
FIG. 5 is a second housing half in cross-sectional view.

FIG. 5 shows in a sectional view the second housing half 3 with its outlet tube 14 and outlet 15, and the second lipped sealing ring 13 with its cavity 17, from which the outlet tube 15 discharges through an opening 16. A recess 21b is provided for reception of an attachment, such as a t-shaped attachment 20, of the gasket 4, which in one embodiment together with the recess 21a of the first housing half 2, may hold or secure the t-shaped attachment 20. The basic form of the second housing half 3 may correspond largely to that of the first housing half 2, as can be seen in particular from FIGS. 6 and 7. The second housing half 3 has a circular collar 30 for a clamp connection with the first housing half 2, which interlocks into the existing recess 25 of the first housing half 2. The collar 30 is formed by a rib 31 about the radial surface 32. The clamping connection between the first housing half 2 and the second housing halve 3 may be by tongue and groove joint.

The housing halves may be comprised of polymeric materials that are generally medically accepted, e.g. polystyrenes, styrenic copolymers (A.B.S.) or to polycarbonates. The interlocking of the housing halves 2, 3 may be by ultrasonic welding or use of medically approved adhesives (e.g. ultra-violet curing adhesives) or a combination thereof. The clamped interfaces between the gasket 4 and housing halves 2, 3 that is outboard of chamber 12 may also be by means of ultrasonic welding or use of medically approved adhesives.

Figure 6:
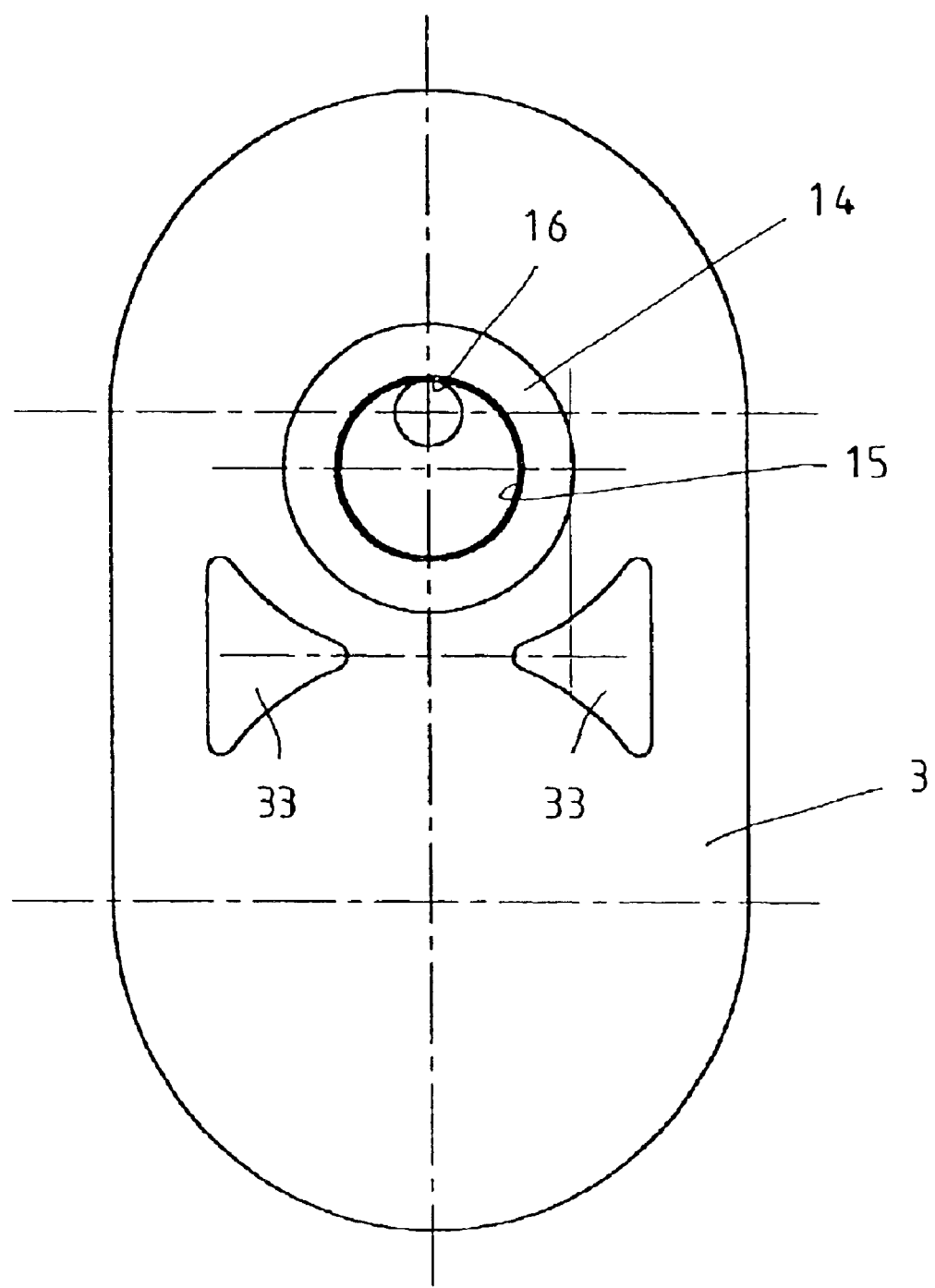
FIG. 6 is a planar view of the exterior of the housing half of FIG. 5.
Figure 7:
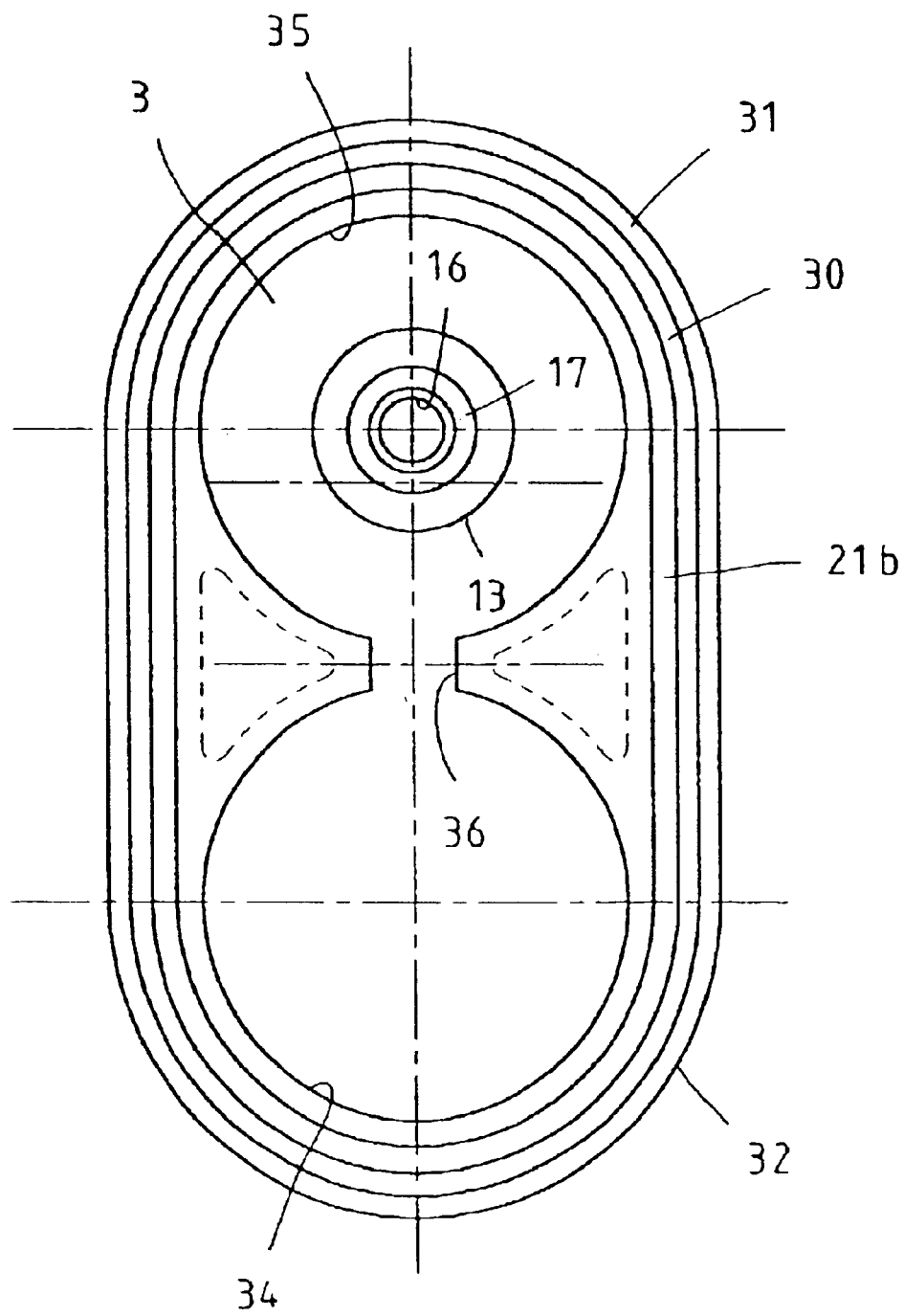
FIG. 7 is a planar view of the interior of the housing half of FIG. 5.

FIGS. 6 and 7 show planar views of the interior and exterior of the second housing half 3. In the exterior of housing half 3, recesses 33 may be formed in approximate triangle shape, while on the inside the pressure chamber 12 may be formed by two ring-shaped recesses 34, 35, and the two recesses 34, 35 are connected with each other by way of an opening 36.

FIG. 8 shows a gasket 4 in plan view and FIG. 9 shows gasket 4 in sectional view. Gasket 4 may be formed in single-piece with a t-shaped attachment 20 about its border. The attachment 20 may rest after assembly in a recess of the two housing halves. The existing opening 11 of gasket 4 comes to rest after assembly, preferably centrally, within the lipped sealing ring 9. To prevent a stress or deformation of the gasket 4, reinforcement ribs, such as integrally molded ribs 41, 42, may be included, which are adapted to the form of the pressure chambers of the two housing halves and serve to facilitate assembly and/or bring about an additional seal toward the housing halves 2, 3, so that the infusion fluid does not pass by the gasket to another pressure chamber or an antechamber. Gasket 4 may be unitary or comprised of multiple components and may be manufactured from a sheet of liquid silicon, silicone or natural rubber or a strip of liquid silicone, silicon or natural rubber, or molded into a preferred shape using such materials.

Embodiments may include a check valve assembly comprising housing halves, defining a pressure chamber, and a gasket provided therebetween for sealing the inlet and outlet tubes. On one side of the gasket is a first lipped sealing ring and on the opposite side thereof a second lipped sealing ring are disposed and the gasket is tensioned over each ring. Alternatively the possibility exists of constructing two pressure chambers communicating via a junction opening, in which at least one single-piece or two separate gaskets are tensioned over a first and second lipped sealing ring, whereby the two lipped sealing rings are in turn arranged at both sides of the gaskets or the junction opening is constructed in such a way that it discharges one time below and one time above the gasket. By means of the gaskets a sealing engagement of the lipped sealing ring occurs, which are with the inlet and/or outlet tubes and in case of the occurrence of vacuum makes possible a sealing toward the lipped sealing rings. On the basis of the alternating sealing engagement of the lipped sealing rings by at least one gasket it is assured that in case of an excess pressure at the outlet tube only a lifting of the gasket at the lipped sealing ring allocated to the outlet tube takes place, while on the other hand the gasket on the second lipped sealing ring is pressed due to the prevailing excess pressure and thus a closure of the inlet tube occurs.

Embodiments may further include the inlet tube discharges into an antechamber, in communication which the first lipped sealing ring is constructed with a closed cavity which is overlied by a gasket that borders the pressure chamber, while the outlet tube within a second lipped sealing ring discharges into the pressure chamber of the housing where a gasket bordering the pressure chamber lies, whereby opposite the second lipped sealing ring a second antechamber bordered by the gasket is constructed, which is supplied with atmospheric pressure by means of a housing opening. The infusion fluid can flow into the antechamber through the inlet tube and lift the gasket adjacent to the first lipped sealing ring, in which in a further embodiment of the invention in the area of the first lipped sealing ring an opening is present, which is constructed centered and lying within the first lipped sealing ring, so that the pressure chamber is sealed across from the antechamber. The flowing infusion fluid lifts this gasket up from the lipped sealing ring and can flow through the existing opening into the pressure chamber of the housing, whereby as a result of the arrangement of the lipped sealing ring on the basis of the existing excess pressure the present single-piece or two-piece gasket is lifted by the second lipped sealing ring, so that a connection to the outlet tube occurs. This is a normal process of flow of the infusion fluid for the case that a sufficient static excess pressure occurs at the inlet tube. If on the other hand there is a vacuum at the inlet tube, the existing gasket closes the first lipped sealing ring by means of the suction effect, thus bringing about an interruption of the flow. The same thing happens when there is vacuum at the outlet tube, since the gasket is supplied with atmospheric pressure in the area of the first lipped sealing ring due to an existing housing opening. For the case that excess pressure should occur at the outlet tube, it will only reach the pressure chamber via the second lipped sealing ring and the sealing gasket and thus presses the existing gasket on the basis of the existing excess pressure directly on the first lipped sealing ring, so that a flow from the inlet tube to the outlet tube is prevented.

Embodiments may further include a gasket area enclosed by the first and second lipped sealing rings that may be smaller than the remaining area of the adjacent gasket portion and that the opening and/or closing pressure can be adjusted by means of the ratio of the enclosed area within the lipped sealing ring to the remaining area of the adjacent gasket area. A gasket, preferably single-piece, is provided for each of the constructed pressure chambers. Alternatively, there is the possibility of using a two-piece gasket, which for example is utilized by two pressure chambers, whereby the two self-contained pressure chambers are connected to each other by means of a junction opening.

Embodiments may also include a check valve assembly with the border of the gasket furnished with a preferably t-shaped (in cross-section) attachment, which comes to rest in a recess of the housing and is preferably integral with the gasket. The t-shaped attachment makes possible a simple attachment option of the one, or if necessary, both gaskets within the housing, whereby the t-shaped attachment comes to rest in a correspondingly designed recess and thus provides a sufficient guarantee for a secure seat of the utilized gaskets. For the improvement of the gasket seat it is further provided that the gasket has in the region of the junction opening one or more reinforcement ribs such as a one or two-sided integrally molded cross-piece rib, which with regard to the form is adapted to the edge of the housing half and/or the pressure chambers. The housing is preferably two-piece in design and held together by means of a clamping groove and tongue joint, whereby through the designed gasket and the two-piece housing form a simple construction may be obtained. The inlet and/or outlet tubes can be arranged vertically to the housing, however, there is also the possibility of arranging them nearly parallel to the housing by means of a bend or elbow and thus creating an efficient and compact housing package.

One of ordinary skill in the art will readily appreciate that by way of the foregoing construction, the opening and/or closing pressure of the check valve can be adjusted by means of the ratio of the enclosed area of the adjacent gasket portions within the lipped sealing rings 9, 13 to the remaining area of the adjacent gasket portions. One of ordinary skill in the art will also readily appreciate that the inlet tube 5 and/or the outlet tube 14 can be arranged not only generally perpendicular to the gasket 4, but also parallel to the gasket 4, or any angle therebetween, with an appropriately angled intermediate elbow or the like.

The disclosed embodiments of the check valve are of simple construction, yet provide a reliable check valve for operating pressures to which it is suited. It is believed that with the construction of these check valves as disclosed, the tension in the gasket can be accurately predetermined and provide automatic stoppage of fluid flow at predetermined fluid pressure differentials between inlet and outlet. In this manner, the present invention avoids complicated designs and yet may result in reliably achieving the above-noted check valve functionality. Further, the design of the above-described embodiments avoids complicated assembly methods by way of limiting the number of highly toleranced dimensions or assembly methods and the like and thus they may lend themselves to assemblage by automated equipment.

It should be appreciated that the apparatus of the present invention is capable of being incorporated in the form of a variety of embodiments, only one of which has been illustrated and described above. The invention may be embodied in other forms without departing from its spirit or essential characteristics. The described embodiment is to be considered in all respects only as illustrative and not restrictive, and the scope of the invention is, therefore, indicated by the appended claims rather than by the foregoing description. All changes which come within the meaning and range of equivalency of the claims are to be embraced within their scope.

I claim:

1. A low pressure check valve for use in an infusion set having infusion fluid comprising:
   (a) a first housing half having an inlet and first lipped sealing ring, the exterior of the first lipped sealing ring in communication with the inlet;
   (b) a second housing half having an outlet and second lipped sealing ring, the interior of the second lipped sealing ring in communication with the outlet;
   (c) a gasket with a first portion overlying the first lipped sealing ring and having at least one opening communicating with the interior of the first lipped sealing ring, and another portion overlying the second lipped sealing ring;
   (d) means for sealing the first and second housing halves together and clamping the gasket portions therebetween; and
   (e) means for tensioning the gasket portions over the first lipped sealing ring and the second lipped sealing ring, thereby forming a pressure chamber in communication with the second lipped sealing ring exterior and the first lipped sealing ring interior via the one or more gasket openings;
   whereby infusion fluid flow in the pressure chamber is interrupted by the gasket portion engaging the first lipped sealing ring when the fluid pressure at the inlet is less than the fluid pressure of the pressure chamber, or by the gasket portion engaging the second lipped sealing ring when the fluid pressure at the outlet is less than the fluid pressure of the pressure chamber, or by the gasket portion engaging the first lipped sealing ring when there is a higher pressure at the outlet and pressure chamber as compared to the pressure at the inlet.

2. The check valve of claim 1 wherein the pressure chamber defined by the housing halves comprises two sub-chambers and a junction opening therebetween, and the first lipped sealing ring and second lipped sealing ring are not coaxial.

3. The check valve of claim 2, further comprising the first housing half defining an antechamber intermediate the inlet and first lipped sealing ring and in communication with the inlet, whereby the antechamber is sealed from the pressure chamber when the gasket engages the first lipped sealing ring.

4. The check valve of claim 3, further comprising the first housing half defining an antechamber in communication with ambient and not in communication with the inlet, wherein the gasket portion is intermediate the antechamber and the second lipped sealing ring, whereby the antechamber remains at ambient pressure during operation of the check valve.

5. The check valve of claim 4, wherein the gasket portion area adjacent the first lipped sealing ring interior is less than the gasket portion area adjacent the first lipped sealing ring exterior, and gasket portion area adjacent the second lipped sealing ring interior is less than the gasket portion area adjacent the second lipped sealing ring exterior.

6. The check valve of claim 5, wherein the gasket includes an attachment portion, and one or both housing halves include a recess that accommodates the attachment portion.

7. The check valve of claim 6, at least one gasket portion further comprising at least one reinforcement rib adapted to engage either the first housing half or the second housing half, whereby placement of the gasket portion overlying the adjacent first or second sealing ring is assured.

8. The check valve of claim 1, further comprising the first housing half defining an antechamber in communication with ambient and not in communication with the inlet, wherein the gasket portion is intermediate the antechamber and the second lipped sealing ring, whereby the antechamber remains at ambient pressure during operation of the check valve.

9. The check valve of claim 8, wherein the gasket portion area adjacent the first lipped sealing ring interior is less than the gasket portion area adjacent the first lipped sealing ring exterior, and gasket portion area adjacent the second lipped sealing ring interior is less than the gasket portion area adjacent the second lipped sealing ring exterior.

10. The check valve of claim 9, wherein the gasket includes an attachment portion, and one or both housing halves include a recess that accommodates the attachment portion.

11. The check valve of claim 10, at least one gasket portion further comprising at least one reinforcement rib adapted to engage either the first housing half or the second housing half, whereby placement of the gasket portion overlying the adjacent first or second sealing ring is assured.

12. The check valve of claim 8, wherein the gasket includes an attachment portion, and one or both housing halves include a recess that accommodates the attachment portion.

13. The check valve of claim 12, at least one gasket portion further comprising at least one reinforcement rib adapted to engage either the first housing half or the second housing half, whereby placement of the gasket portion overlying the adjacent first or second sealing ring is assured.

14. The check valve of claim 8, the gasket portion further comprising at least one reinforcement rib adapted to engage either the first housing half or the second housing half, whereby placement of the gasket portion overlying the adjacent first or second sealing ring is assured.

15. The check valve of claim 1, wherein the gasket portion area adjacent the first lipped sealing ring interior is less than the gasket portion area adjacent the first lipped sealing ring exterior, and gasket portion area adjacent the second lipped sealing ring interior is less than the gasket portion area adjacent the second lipped sealing ring exterior.

16. The check valve of claim 15, wherein the gasket includes an attachment portion, and one or both housing halves include a recess that accommodates the attachment portion.

17. The check valve of claim 16, at least one gasket portion further comprising at least one reinforcement rib adapted to engage either the first housing half or the second housing half, whereby placement of the gasket portion overlying the adjacent first or second sealing ring is assured.

18. The check valve of claim 1, wherein the gasket includes an attachment portion, and one or both housing halves include a recess that accommodates the attachment portion.

19. The check valve of claim 18, the gasket portion further comprising at least one reinforcement rib adapted to engage either the first housing half or the second housing half, whereby placement of the gasket portion overlying the adjacent first or second sealing ring is assured.

20. The check valve of claim 1, the gasket portion further comprising at least one reinforcement rib adapted to engage either the first housing half or the second housing half, whereby placement of the gasket portion overlying the adjacent first or second sealing ring is assured.

21. The check valve of claim 20, wherein the gasket includes an attachment portion, and one or both housing halves include a recess that accommodates the attachment portion.

* * * * *